United States Patent [19]

Hsu

[11] Patent Number: 4,855,485

[45] Date of Patent: Aug. 8, 1989

[54] PROCESS FOR PRODUCTION OF CINNAMATES

[75] Inventor: Chao-Yang Hsu, Media, Pa.

[73] Assignee: Sun Refining and Marketing Company, Philadelphia, Pa.

[21] Appl. No.: 45,507

[22] Filed: May 4, 1987

Related U.S. Application Data

[63] Continuation-in-part of Ser. No. 684,822, Dec. 21, 1984, Pat. No. 4,737,591.

[51] Int. Cl.$^4$ .............................................. C07C 69/76
[52] U.S. Cl. .................................... 560/104; 562/406; 568/311
[58] Field of Search ....................... 560/104; 562/406; 568/37

[56] References Cited

FOREIGN PATENT DOCUMENTS 152075 2/1985 European Pat. Off. ............ 560/104
186349 2/1986 European Pat. Off. ............ 560/104
57-021342 4/1982 Japan .................................. 560/104

*Primary Examiner*—Paul J. Killos
*Attorney, Agent, or Firm*—J. Edward Hess; Donald R. Johnson

[57] ABSTRACT

In the process of preparing esters of cinnamic acid by reacting a styrene compound with carbon monoxide, oxygen, and an aliphatic alcohol in the presence of a catalyst, the improvement comprising using less than a stoichiometric amount of a dehydrating agent to increase the yield and selectivity of the reaction products.

8 Claims, No Drawings

PROCESS FOR PRODUCTION OF CINNAMATES

BACKGROUND OF THE INVENTION

This application is a continuation-in-part of U.S. application Ser. No. 684,822, filed Dec. 21, 1984 in the name of C. Y. Hsu now U.S. Pat. No. 4,737,591.

The present invention relates to an improved process for preparing cinnamates by oxidative carbonylation of styrene compounds.

Cinnamic acid and cinnamates are used as a material for perfumes, as a cinnamic aldehyde, cyclamen aldehyde, beta-amyl cinnamic aldehyde, and the like.

Cinnamates are made conventionally through a Claisen condensation from benzaldehyde and alkylacetate in the presence of sodium alkoxide, as shown in Equation I:

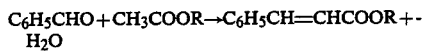

$$C_6H_5CHO + CH_3COOR \rightarrow C_6H_5CH=CHCOOR + H_2O \qquad (I)$$

Another method of making cinnamates is by esterification of cinnamic acid, as shown in Equation II:

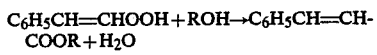

$$C_6H_5CH=CHOOH + ROH \rightarrow C_6H_5CH=CHCOOR + H_2O \qquad (II)$$

Recently, several methods for preparing cinnamates have been reported, employing palladium catalysts. Heck et al., *J. Amer. Chem., Soc.* 91, 6707 (1969) and Patel et al., *J. Org. Chem.*, 42, 3903 (1977), show methods of preparing cinnamates using palladium acetate-tertiary phosphine as a catalyst in the reaction of phenyl bromide and an alkyl acrylate. This reaction has the drawback of involving rather expensive raw materials. This reaction is shown in Equation III:

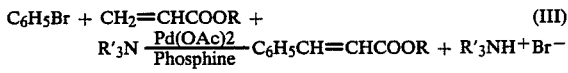

$$C_6H_5Br + CH_2=CHCOOR + R'_3N \xrightarrow[\text{Phosphine}]{Pd(OAc)2} C_6H_5CH=CHCOOR + R'_3NH^+Br^- \qquad (III)$$

Other cinnamates, such as methyl cinnamate, can be synthesized in a palladium-catalyzed reaction by reacting styrene with carbon monoxide and methanol, as reported by J. K. Stille and his coworkers, *J. Amer. Chem. Soc.*, 98, 1806 (1976) and 98, 1810 (1976); *J. Org. Chem.*, 44, 3474 (1979); and by G. Cometti and G. P. Chiusoli in *J. Organometal. Chem.*, 181, C14 (1979).

In Stille's method, methyl cinnamate was obtained only in small amounts, with dimethyl phenylsuccinate being the major product. Additionally, a stoichiometric amount of copper (II) salt was required in this reaction. The method of Cometti and Chiusoli has the same disadvantage of using a large excess of copper (II) salt as an oxidant. Thus, both methods are unsuitable for industrial applications.

Many patents disclose oxidative carbonylation of olefins to alpha, beta-unsaturated esters by reacting an olefin with carbon monoxide, oxygen, and an alcohol in the presence of a catalytic amount of palladium and copper salts, cf U.S. Pat. Nos. 3,381,030; 3,397,225; 3,397,226; 3,530,168; 3,621,054. None of these patents discloses a satisfactory method for producing cinnamates.

Moreover, U.S. Pat. No. 3,381,030, while stating that substantial quantities of dehydrating agent are not necessary in the oxidative carbonylation of olefins to acids, nevertheless teaches throughout the specification that the reaction should be maintained under anhydrous conditions, preferably in the absence of even the slightest amounts of water (col. 3, lines 1 and 2), and that any quantities of water should be removed (col. 7, line 46). In addition, it will be seen that all of the examples use substantial amounts of acetic anhydride dehydrating agent. Where none is used (Ex. 3, line 56) significant amounts of by-product are formed. Moreover, when the amount of dehydrating agent is reduced significantly (Ex. 4), the yield of desired product is reduced by about half. Thus, this patent teaches that large amounts of dehydrating agent are necessary, and that the presence of any water is unacceptable.

Similarly, U.S. Pat. No. 3,346,625 teaches that in the oxidative carbonylation of olefins to acids, anhydrous conditions must be maintained, even though substantial quantities of dehydrating agent are not necessary. This patent further teaches that when no dehydrating agent is used (col. 7, line 12), only minor amounts of desired product are formed. Therefore, it is taught that significant amounts of dehydrating agent are necessary, that only anhydrous conditions are acceptable, and that in the absence of a dehydrating agent, virtually all the products are by-products.

U.S. Pat. No. 3,397,225 also teaches the oxidative carbonylation of olefins in which no oxygen is employed except to regenerate the catalyst. As in the above patents it is taught that the reaction must be carried out under anhydrous conditions, and various dehydrating agents for this purpose are disclosed. Thus, again, it is shown to be essential that anhydrous conditions be maintained.

In U.S. Pat. No. 3,397,226 substantially the same process and conditions as in closely related U.S. Pat. No. 3,397,225, above, are taught, including the need for carrying out the reaction in anhydrous conditions. Moreover, in Example 3 of this patent there is disclosed the use of amounts of dehydrating agent triethyl orthoformate (200 parts) with an equal amount of ethanol, which demonstrates the use of stoichiometric amounts or more of dehydrating agent.

In addition to these differences in the above four patents, none of them teach or suggest that by the use of less than stoichiometric amounts of dehydrating benefits, unusual benefits in the form of good yield and selectivity for the desired products may be obtained.

Two Japanese patent application Nos. 21,342 (1982) and 21,343 (1982), disclose that low yields of methyl cinnamate could be achieved through oxidative carbonylation of styrenes, provided that an excess amount of dehydrating agent relative to the amount of styrene employed is used in the reaction. Because the dehydrating agent is an expensive component of the reaction, industrial application of this method is limited. It was disclosed in these two Japanese applications that when styrenes were allowed to react with aliphatic alcohols, carbon monoxide, and oxygen in the presence of palladium and a dehydrating agent, cinnamates could be obtained with a high reaction rate and a high yield. However, this reaction has the disadvantage of requiring an excess of dehydrating agent, which makes the reaction unfeasible for industrial use.

SUMMARY OF THE INVENTION

Cinnamates can be produced by the oxidative carbonylation of styrene compounds according to the following reaction:

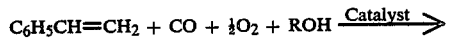

Thus, it has been unexpectedly found that when a styrene compound is reacted with carbon monoxide, oxygen, and an aliphatic alcohol and in the presence of a catalyst, wherein a dehydrating agent is used in less, and preferably significantly less than the stoichiometric amounts of the aforesaid prior art, i.e., in amounts defined below, there is obtained increased yield and selectivity of the cinnamate ester product, and acetophenone by-product. Surprisingly, this is so even though water formed in the course of the reaction is present; this water need not be removed. That is to say, the reaction need not be anhydrous, as taught by the prior art.

More specifically, the amount of dehydrating agent which may be used in accordance with this invention to increase the selectivity and yield, of the reaction is up to about 50 mole percent based on the amount of styrene employed. The minimum amount, on the other hand, is that quantity which provides at least a measurable increase in selectivity for the cinnamate product and acetophenone compared to using no dehydrating agent at all. Within these general ranges the desired amount can be determined routinely by those skilled in the art, but is preferably 10–40%, more preferably 25–40%.

Examples of dehydrating agents that can be used include dimethoxymethane, other acetals, 2,2-dimethoxypropane, other ketals, methyl orthoformate, ethyl orthoformate, isopropyl orthoformate, t-butyl orthoformate, other ortho-esters of carboxylic acids, dimethoxycyclohexane, other dialkoxycycloalkanes, triethyl borate, trioctyl borate, other orthoborates, and the like.

The general formula for styrenes used in the present invention can be represented by the following structure:

wherein $R_1$ and $R_2$ can be hydrogen, halogen, hydroxyl, alkyl, alkoxyl, aryl, aryloxy, or nitro functional groups. $R_3$ is an alkyl group of one to six carbon atoms. Specific examples for styrenes are styrene, alpha-methyl styrene, p-chloro styrene, p-nitro styrene, m-methoxy styrene, p-phenyl styrene, beta-methyl-p-isopropylstyrene, beta-amylstyrene, and the like.

The aliphatic alcohols for use in the reaction according to the present invention include aliphatic alcohols having from one to six carbon atoms, such as methanol, ethanol, propanol, isopropanol, t-butanol, n-butanol, hexanol, and the like. It is also possible to use compounds capable of yielding the aforementioned alcohols in reaction systems containing acetals, ketals, orthoesters of carboxylic acids, dialkylcycloalkanes, orthoboric acid esters, and the like.

Carbon monoxide and oxygen for this reaction can be used either in the pure state or can be mixed with nitrogen, argon, or other inert gases as the diluents. Air can be used as the oxygen source. In general, carbon monoxide and oxygen can be charged into the reactor through a separated inlet system or can be charged as a mixture with or without inert gases as the diluents. The partial pressure of carbon monoxide or oxygen is adjusted so that the gas mixture in the reactor system is outside the explosive range.

Catalysts which may be employed for the oxidative carbonylation of styrene are, as stated above, metal compounds such as palladium compounds, preferably palladium salts, in combination with other compounds; however, as described below, other metals such as rhodium or platinum compounds may be used instead of palladium.

One preferred catalyst system which may be employed herein consists of a palladium salt and a copper salt. The palladium salt can be palladium chloride, palladium bromide, palladium iodide, palladium nitrate, or other divalent palladium salts such as palladium acetate, palladium benzoate, palladium acetylacetonate, palladium trifluoroacetate, palladium oxide, potassium tetrabromopalladate, sodium tetrachloropalladate, and the like. Any other forms of palladium which can form palladium (II) salt under the reaction conditions can be used. Examples are supported palladium such as palladium on carbon, palladium on silica, or palladium on alumina, palladium on silica-alumina, magnesia, titania, kieselguhr, active charcoal, graphite, etc., palladium black, and palladium sponge. Further examples of useful palladium compounds are palladium alpha-picolinate, carboxylates of divalent palladium, bis (acetylacetonato) palladium, bis (triphenylphosphine) dichloro palladium, cyclooctadiene dichloropalladium, tetramine dichloro palladium, and the like.

Alternatively, as stated above, other metal compounds besides palladium which may be used in the catalysts of this process include, for example, rhodium or platinum compounds, preferably in their salt form, in combination with other compounds such as copper salts.

The copper salts which may be used can be either copper (I) or copper (II) salts. Examples of these salts are copper (I) or (II) halides such as copper (II) fluoride, copper (I) chloride, copper (II) chloride, copper (I) bromide, copper (II) bromide, copper (I) iodide, and other non-halide coppers salts such as copper (II) nitrate, copper (II) acetate, and copper (II) sulfate.

The reaction temperatures can range from about 25° to 250° C., and the preferred temperature range is from about 50° C. to about 150° C.

Reaction pressures can range from about 1 to about 1500 psi, although ranges in the amount of about 50 to about 750 psi are preferred.

The gas composition, the molar ratio of carbon monoxide to oxygen, can range broadly from about 0.1 to 20. A molar ratio of carbon monoxide to oxygen of from about 0.25 to 10 is preferred.

A preferred catalyst composition can range from a molar ratio of copper to metal compound of about 1 to 50, although a molar ratio of copper to metal compound of about 2.5 to 20 is preferred.

The molar ratio of styrene to metal compound can range from about 10,000 to 10. A molar ratio of styrene to metal compound of about 1000 to 25 is preferred.

The molar ratio of alcohol to styrene can range from 500 to 1, although a molar ratio of alcohol to styrene of from about 10 to about 1 is preferred.

DETAILED DESCRIPTION OF THE INVENTION

The following examples show the benefits of producing cinnamates according to the present invention.

EXAMPLE I

In this example, a stoichiometric amount of dehydrating agent was used in the reaction. The procedure was carried out as follows: Styrene (53.0 g, 510 mmole), methanol (96.6 g, 3024 mmole), 503 mmole of 2,2-dimethoxypropane (as dehydrating agent), palladium (II) chloride (0.444 g, 2.5 mmole), and copper (I) chloride (2.475 g, 25 mmole) were charged into a 300 ml Hastelloy autoclave. After the autoclave was sealed, it was purged with a gas mixture containing 13% carbon monoxide in air by bubbling the gas mixture through the liquid contents of the autoclave while stirring for about 10 minutes. After that, the gas flow was adjusted to a 500 ml/min. flow rate, and the pressure in the reactor was adjusted to 500 psig with a back pressure regulator. The autoclave was then heated to 100° C., and the reaction was kept at this temperature for 4.0 hours. The conversion of styrene was 100% with 50.7% selectivity to methyl cinnamate (259 mmole) and 4.3% selectivity to acetophenone (22 mmole).

EXAMPLE II

The procedure of Example I was repeated, except that only 180 mmole of 2,2-dimethoxypropane was used (36 mole % based on styrene) The conversion of styrene was 100% with 53.8% selectivity to methyl cinnamate (274 mmoles), and 18.5% selectivity to acetophenone (93 mmole).

It can be seen from a comparison of Example I and II that a less than stoichiometric amount of dehydrating agent relative to styrene increases the yield and selectivity of methyl cinnamate and acetophenone over that obtained with a stoichiometric amount of dehydrating agent.

The procedures can be used with alcohols such as ethanol, propanol, isopropanol, the butanols, pentanols, and hexanols to produce the corresponding cinnamates. The alcohol is used in quantities to give approximately 3000 mmole of alcohol to approximately 500 mmole of styrene. Where alcohols other than methanol are used, a small amount of dehydrating agent, up to 50 mole percent based on the amount of styrene, can be used to increase the selectivity and yield of the desired reaction products.

The catalysts that can be used in the process of the present invention include any combination of palladium, rhodium or platinum compounds, preferably palladium (II) and copper. The valence of copper can be either I or II. The copper can be present in the form of a salt of either copper (I) or copper (II). The palladium can be present in the form of a salt or of any other compound that, under the reaction conditions, will yield of palladium (II) compound, including palladium black and palladium complex salts.

What is claimed is:

1. A process for the production of methyl cinnamate and acetophenone which comprises the oxidative carbonylation of styrene with carbon monoxide, oxygen, and methanol in the presence of a catalyst, and in the presence of dehydrating agent in less than a stoichiometric amount.

2. The process of claim 1 wherein the amount of dehydrating agent employed is up to about 50 mole percent based on the amount of styrene used.

3. The process of claim 1 wherein the dehydrating agent is selected from the group consisting of dimethoxymethane, 1,1,2-trimethoxyethane, 2,2-diethoxypropane, 2,2-dimethoxypropane, methyl orthoformate, ethyl orthoformate, isopropyl orthoformate, t-butyl orthoformate, dimethoxycyclohexane, triethyl borate, and trioctyl borate.

4. The process of claim 1 wherein the dehydrating agent is a 2,2-dialkoxyalkane.

5. The process of claim 4 wherein the dehydrating agent is 2,2-dimethoxypropane.

6. The process according to claim 1 wherein the catalyst is a metal compound selected from the group consisting of palladium, rhodium, and platinum compound, and a copper salt.

7. The process according to claim 6 wherein the metal compound is a halide, carboxylate or dicarboxylate.

8. The process of claim 1 wherein the catalyst is a palladium salt and a copper salt.

* * * * *